(12) United States Patent
Yamauchi (10) Patent No.: US 8,107,072 B2
(45) Date of Patent: Jan. 31, 2012

(54) ATOMIC ABSORPTION SPECTROPHOTOMETER

(75) Inventor: Kazuo Yamauchi, Ibaraki (JP)

(73) Assignee: Shimadzu Corporation, Kyoto (JP)

( * ) Notice: Subject to any disclaimer, the term of this patent is extended or adjusted under 35 U.S.C. 154(b) by 297 days.

(21) Appl. No.: 12/574,213

(22) Filed: Oct. 6, 2009

(65) Prior Publication Data

US 2010/0091277 A1   Apr. 15, 2010

(30) Foreign Application Priority Data

Oct. 9, 2008 (JP) .................. 2008-262414

(51) Int. Cl.
  *G01J 3/08*  (2006.01)
  *G01J 3/42*  (2006.01)
  *G01N 21/31* (2006.01)
(52) U.S. Cl. .................. 356/323; 356/307
(58) Field of Classification Search ............. 356/307, 356/323, 325
  See application file for complete search history.

(56) References Cited

U.S. PATENT DOCUMENTS
4,332,470 A * 6/1982 Chamran et al. ............. 356/325

FOREIGN PATENT DOCUMENTS
JP       2003-14631 A    1/2003
* cited by examiner

*Primary Examiner* — F. L. Evans
(74) *Attorney, Agent, or Firm* — Sughrue Mion, PLLC (57) ABSTRACT

The present invention has been accomplished to provide an atomic absorption spectrophotometer capable of obtaining measurement data always in the state where the lowest detection limit performance is optimized, without depending on the frequency of the power supply. In a control program which runs on the microcomputer chip 42 mounted on the atomic absorption spectrophotometer 110, a plurality of lighting periods of the light sources 11 and 12 and extraction periods of the sampling data are memorized, whose lowest detection limit performance are optimized for the frequencies (50 Hz and 60 Hz) of the AC power source for driving the AC motor 22. In using the apparatus, by the control program, the frequency of the power source used in this apparatus is identified, the lighting period and sampling data extraction period corresponding to the identified frequency and the measurement mode that a user of the apparatus has previously set are selected from among a plurality of memorized values, and the appropriate lighting period is set to the hardware (PLD 43). Accordingly, without depending on the frequency, it is possible to obtain measurement data always in the state where the lowest detection limit performance is optimized.

4 Claims, 8 Drawing Sheets

ATOMIC ABSORPTION SPECTROPHOTOMETER

The present invention relates to an atomic absorption spectrophotometer. More precisely, it relates to an atomic absorption spectrophotometer using a double beam optical system.

BACKGROUND OF THE INVENTION

Figure 1:
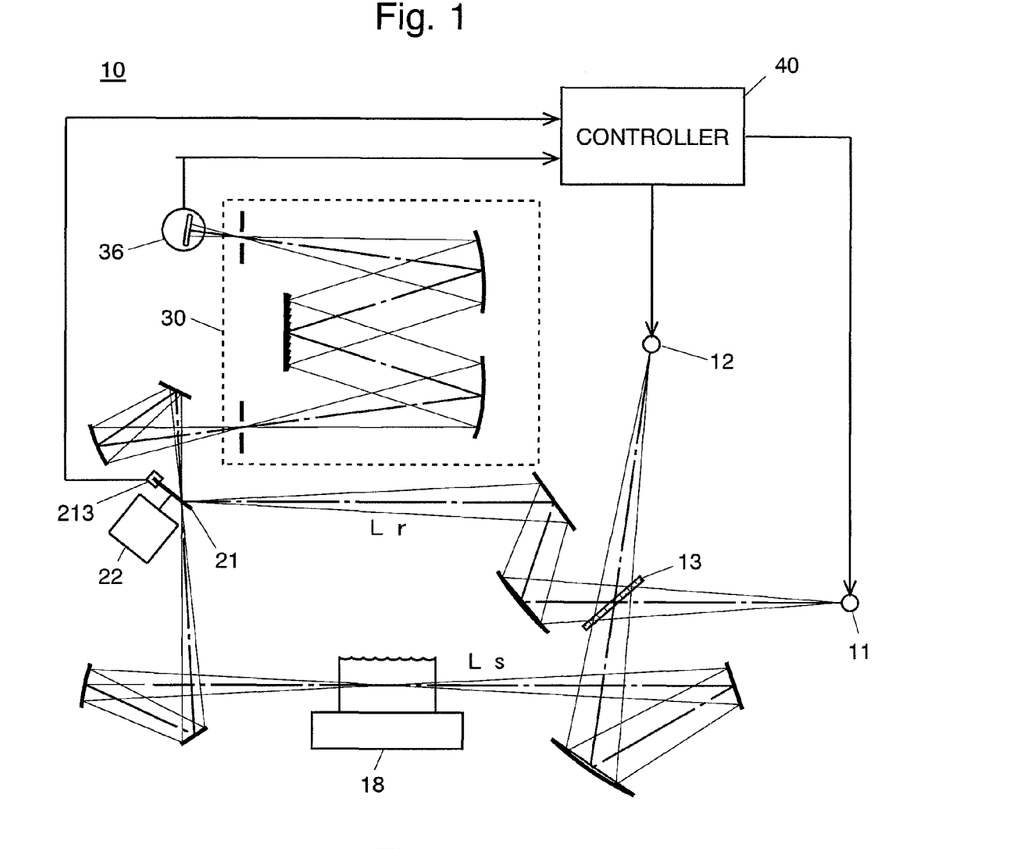
FIG. 1 is a schematic configuration diagram of an atomic absorption spectrophotometer using a double beam optical system.

FIG. 1 is a schematic configuration diagram of an atomic absorption spectrophotometer 10 using a double beam optical system. The atomic absorption spectrophotometer 10 is mainly composed of: a hollow cathode (HC) lamp 11 which is a light source for emitting a light having a bright-line spectrum; a deuterium (D2) lamp 12 which is a light source for emitting a light having a continuous spectrum; a half mirror 13 for dividing the light emitted from each lamp into two directions; an atomization unit 18 for atomizing a sample; and a sector mirror 21 for sending each light divided by the half mirror 13 to the same optical path; a spectroscope 30 for separating the light sent from the sector mirror 21; a detector 36 for detecting the intensity of the separated light; and a controller 40 for performing a transmission of a variety of signals and data processing. For the details, refer to Patent Document 1.

Figure 2:
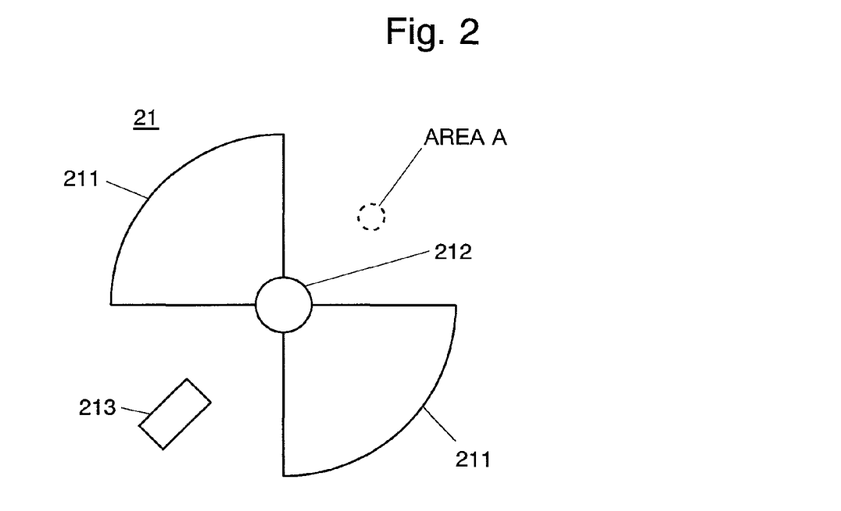
FIG. 2 is a front view of the sector mirror.

FIG. 2 is a front view of the sector mirror 21. The sector mirror 21 is composed of two sector-shaped mirrors 211, each having a central angle of 90°, symmetrically-placed with respect to a shaft 212. A motor 22 is connected to the shaft 212, and the sector mirror 21 is rotated on the shaft 212 by the motor 22. On the rotational course of the mirror 211, a photo interrupter 213 is placed in such a manner as to sandwich the course. The photo interrupter 213 generates detection signals indicating whether the mirror 211 exists at the position, and the detection signals are transmitted to the controller 40.

The light from the light source which reaches the sector mirror 21 has a definite diameter on the sector mirror 21. As shown in FIG. 2, the photo interrupter 213 is placed at the symmetrical position, with respect to the shaft 212, to an area A which corresponds to the cross-section of the light. In this example, it is adjusted that the edges of the mirror 211 reach the area A and the photo interrupter 213 at approximately the same moment. When the edge of the mirror 211 reaches the area A, the state of the detection signal generated from the photo interrupter 213 is changed.

In the atomic absorption spectrophotometer 10, the lights emitted from the HC lamp 11 and the D2 lamp 12 are divided into two directions by the half mirror 13. One of the divided light (sample light Ls) passes through the atomization unit 18, and the other light (reference light Lr) passes through a space out of the atomization unit 18 and then reaches the same area A in the rotating sector mirror 21. In the case where the mirror 211 does not exist at the area A, the sample light Ls passes through the area, and in the case where the mirror 211 exists at the area A, the reference light Lr is reflected there and enters the spectroscope 30. Accordingly, the sample light Ls and the reference light Lr alternately enter the spectroscope 30. The light which has entered the spectroscope 30 is separated and a light having a specific wavelength enters the detector 36. In the detector 36, a detection signal corresponding to the intensity of the entered light is generated, and the detection signal is transmitted to the controller 40. The detection signal received by the controller 40 is analog-to-digital (A/D) converted at predetermined sampling intervals, and the sampling data is recorded in a data memory.

In the atomic absorption spectrophotometer 10 as just described, the absorbance of a sample is obtained as follows.

Figure 3:
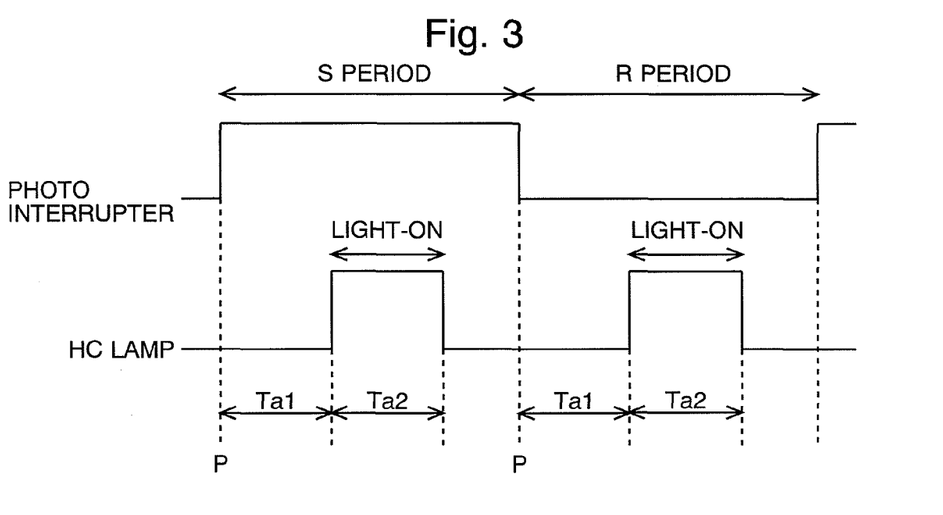
FIG. 3 illustrates a blinking manner of the HC lamp in the Non-BGC-Double measurement mode.

First, an explanation is made for the case where only the HC lamp 11 is used as the light source. (Hereinafter, this case will be called a Non-BGC-Double measurement mode.) FIG. 3 illustrates a blinking manner of the HC lamp 11 in this case. The photo interrupter 213 generates an H level signal while the sample light Ls passes through the sector mirror 21 (S period), and generates an L level signal while the reference light Lr is reflected by the sector mirror 21 (R period). The HC lamp 11 is ON for the second predetermined period Ta2, which has the starting point after the first predetermined time Ta1 has passed from the time point when the S period and the R period are changed to each other, i.e. from the changing point P when the detection signal of the photo interrupter 213 changes. During the other period, the HC lamp 11 remains OFF.

The absorbance $A_H$ in this case is defined by the following equations:

$$A_H = -\log_{10} T_H,$$

$$T_H = (H_S' \times H_{R0}')/(H_R' \times H_{S0}').$$

The absorbance of the sample can be obtained by substituting the values corresponding to the following symbols to these equations.

$H_S$: The average of the sampling data obtained while the HC lamp is ON in the S period.

$DK_S$: The average of the sampling data obtained while the HC lamp is OFF in the S period.

$H_R$: The average of the sampling data obtained while the HC lamp is ON in the R period.

$DK_R$: The average of the sampling data obtained while the HC lamp is OFF in the R period.

$$H_S' = H_S - DK_S$$

$$H_R' = H_R - DK_R$$

$H_{S0}'$: $H_S'$ that has been previously obtained while there was no sample, i.e. while the atomization of the sample was not being performed.

$H_{R0}'$: $H_R'$ that has been previously obtained while there was no sample, i.e. while the atomization of the sample was not being performed.

Figure 4:
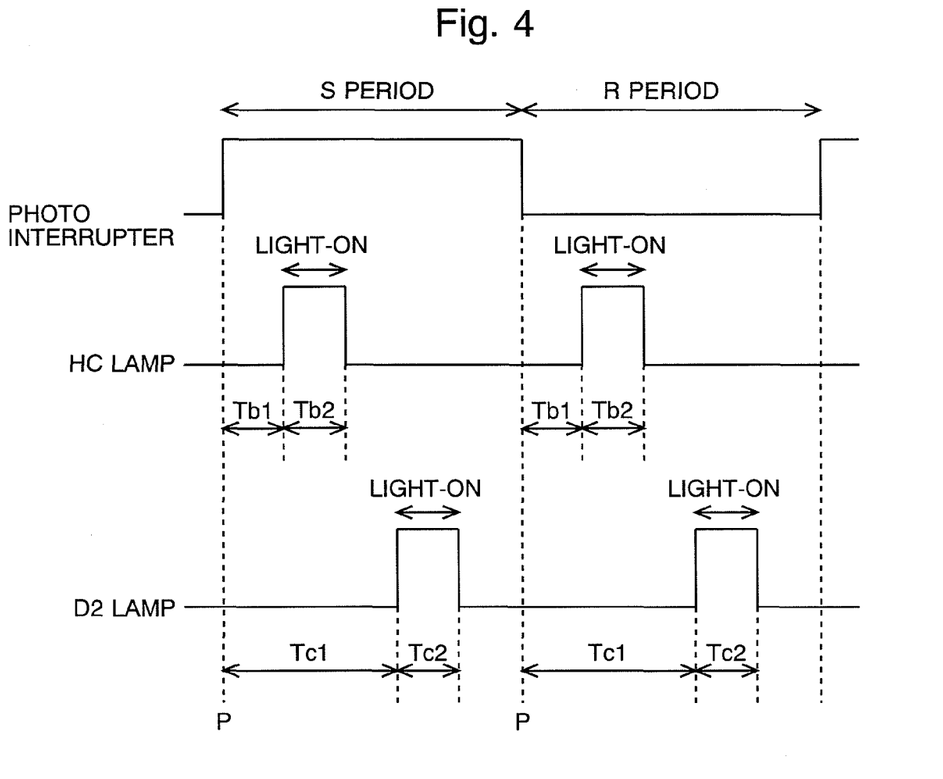
FIG. 4 illustrates a blinking manner of the HC lamp and D2 lamp of the BGC-D2-Double measurement mode.

Next, an explanation is made for the case where a background correction is performed using the D2 lamp 12 as well as the HC lamp 11 as a light source. (Hereinafter, this case will be called a BGC-D2-Double measurement mode.) FIG. 4 illustrates a blinking manner of the HC lamp 11 and the D2 lamp 12 in this case. The photo interrupter 213 generates, as in the aforementioned Non-BGC-Double measurement mode, an H level signal in the S period, and L level signal in the R period. The HC lamp 11 is ON for the fourth predetermined period Tb2, which has a starting point after the third predetermined period Tb1 has passed from the changing point P of the detection signal of the photo interrupter 213, and the HC lamp 11 remains OFF during the other period. The lighting period of the HC lamp 11 and that of the D2 lamp 12 are set not to coincide with each other.

The absorbance $A_{BGC}$ in this case is defined by the following equations:

$$A_{BGC} = -\log_{10} T_{BGC},$$

$$T_{BGC} = (H_S' \times H_{R0}' \times D_R' \times D_{S0}')/(H_R' \times H_{S0}' \times D_S' \times D_{R0}').$$

The absorbance of the sample which is background-corrected by the D2 lamp 12 can be obtained by substituting, to these equations, the values corresponding to the symbols used for obtaining the absorbance in the Non-BGC-Double measurement mode and the values corresponding to the following symbols.

$D_S$: The average of the sampling data obtained while the D2 lamp is ON in the S period.

$D_R$: The average of the sampling data obtained while the D2 lamp is ON in the R period.

$$D_S' = D_S - DK_S$$

$$D_R' = D_R - DK_R$$

$D_{S0}'$: $D_S'$ that has been previously obtained while there was no sample, i.e. while the atomization of the sample was not being performed.

$D_{R0}'$: $D_R'$ that has been previously obtained while there was no sample, i.e. while the atomization of the sample was not being performed.

Patent Document 1: Japanese Unexamined Patent Application Publication No. 2003-14631

In general, as the motor 22 for rotating the sector mirror 21, an alternating-current (AC) motor is used in many cases in order to simplify the configuration, moderate the cost, and reduce the rotational noise as much as possible. And the AC motor is often powered by a commercial AC source. In such a case, the rotational speed of the AC motor is proportional to the alternating frequency of the AC power source, and the rotational speed of the sector mirror is also proportional to the frequency of the AC power source. The lengths of the S period and the R period are inversely proportional to the rotational speed of the sector mirror 21. Therefore, the lengths of the S period and R period are inversely proportional to the frequency of the AC power source.

Figure 5A:
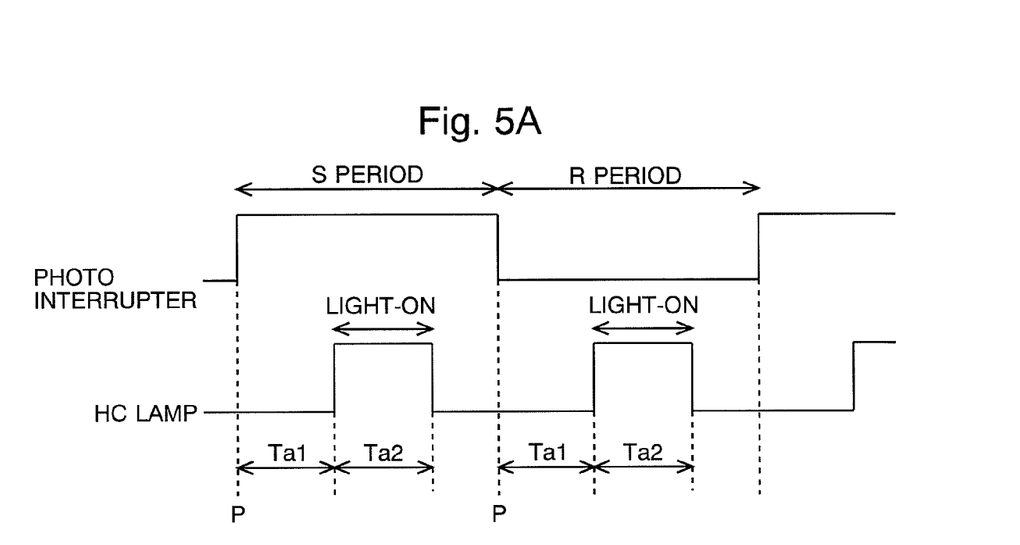
FIG. 5A illustrates a blinking manner of the HC lamp in the Non-BGC-Double measurement mode in the case where the alternating frequency is 60 Hz.
Figure 5B:
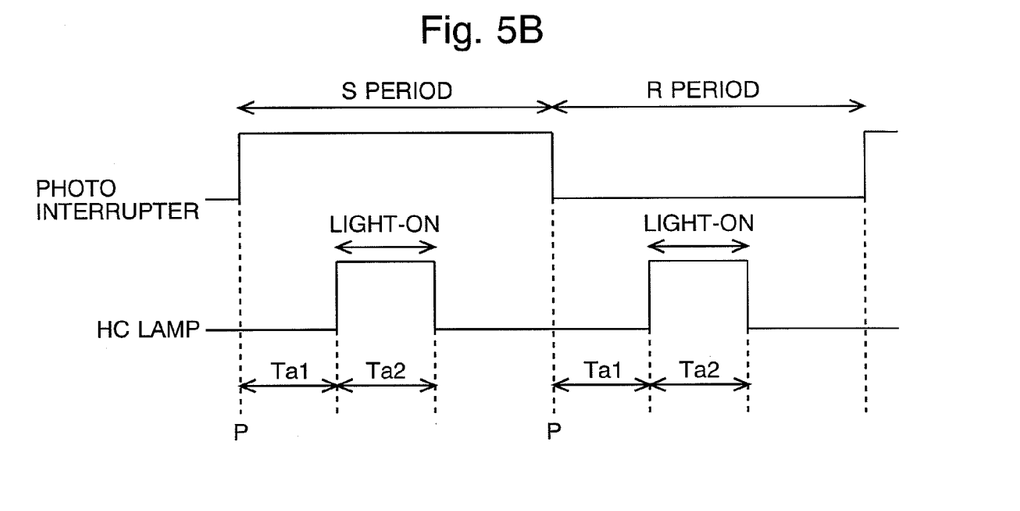
FIG. 5B illustrates that in the case where the frequency is 50 Hz.

FIG. 5 illustrates a blinking manner of the HC lamp 11 in the Non-BGC-Double measurement mode in the cases where the frequency is 60 Hz (FIG. 5A) and 50 Hz (FIG. 5B). The lengths of the S period and the R period are shorter in the case where the frequency is 60 Hz due to the aforementioned reason. Since the HC lamp 11 is set, in each case, to be ON only during the second predetermined period Ta2 which starts at the time point after the predetermined period Ta1 has passed from the changing point P of the detection signal of the photo interrupter 213, the first predetermined period Ta1 and the second predetermined period Ta2 are set for the case of 60 Hz where the interval of blinking is shorter than that of the case of 50 Hz.

However, with such a setting, in the case of 50 Hz where the S period and R period are longer, i.e. in the case where the alternating frequency of the AC power source is lower, the number of blinks of the lamp per unit time decreases. In the meantime, the second predetermined period Ta2 which is the lighting time is set to be a constant value, and therefore in the case where the frequency is low, the total lighting time per unit time becomes shorter and the number of pieces of sampling data obtained while the light is ON decreases. This increases the statistical error of the sampling data, which deteriorates the lowest detection limit performance of elements. This problem also occurs in the BGC-D2-Double measurement mode.

SUMMARY OF THE INVENTION

The present invention has been accomplished to solve the aforementioned problem and the objective thereof is to provide an atomic absorption spectrophotometer capable of obtaining measurement data always in the state where the lowest detection limit performance is optimized, without depending on the alternating frequency of the AC power supply.

To solve the previously-described problems, the present invention provides an atomic absorption spectrophotometer comprising:

a) an optical system for dividing a light emitted from a light source into two directions so that one divided light passes through an atomization unit of a sample and the other divided light passes through the space other than the atomization unit, after that introducing each light into a sector mirror rotated by an alternating-current (AC) motor so that the divided lights alternately enter a spectroscope, and sending a light separated by the spectroscope to a detector;

b) a light source controller for turning ON the light source for a predetermined lighting period, in synchronization with the rotation of the sector mirror; and c) a sampling data extractor for extracting sampling data of a detection signal generated from the detector during a predetermined extraction period, in synchronization with the rotation of the sector mirror;

wherein the atomic absorption spectrophotometer includes:

d) a memory means for memorizing a plurality of setting values of the lighting period and the extraction period, in association with the frequency of an alternating-current power source for driving the alternating-current motor;

e) a frequency identifying means for identifying the frequency of the alternating-current power source; and f) a lighting/extraction period setting means for reading out a setting value from the memory means, corresponding to the frequency identified by the frequency identifying means, and setting, based on the setting value, the lighting period of the light source and the extraction period of the sampling data.

The light source controller in the present invention may turn ON and OFF the light source itself, or may periodically shut out the light emitted from the light source by a shutter or other element.

In the atomic absorption spectrophotometer according to the present invention, a setting value corresponding to the frequency is read out from among a plurality of setting values which have been previously memorized in the memory means, and based on the setting value, the lighting period of the light source and the extraction period of the sampling data are set. Therefore, the lighting period of the light source and the extraction period of the sampling data can be optimally set, even for a different frequency. That is, without depending on the frequency of the AC power supply, the measurement data can always be obtained in the state where the lowest detection limit performance is optimized.

BRIEF DESCRIPTION OF THE DRAWINGS

FIG. 7A is a front view.

EXPLANATION OF THE NUMERALS 10, 110 . . . Atomic Absorption Spectrophotometer
11 . . . HC lamp
12 . . . D2 lamp
13 . . . Half Mirror
18 . . . Atomization Unit
21, 61 . . . Sector Mirror
211, 611 . . . Mirror
212, 612 . . . Shaft
213, 613 . . . Photo Interrupter
22 . . . Motor
30 . . . Spectroscope
31 . . . Entrance Slit
32, 34 . . . Concave Spherical Mirror
33 . . . Plane Diffraction Grating
35 . . . Exit Slit
36 . . . Detector
40, 41 . . . Controller
42 . . . Microcomputer Chip
421 . . . ROM
43 . . . Programmable Logic Device (PLD)
45 . . . Amplifier
46 . . . A/D converter
47 . . . Light Source Drive
50 . . . PC
615 . . . Timing Plate
Lr . . . Reference Light
Ls . . . Sample Light

DETAILED DESCRIPTION OF A PREFERRED EMBODIMENT

Figure 6:
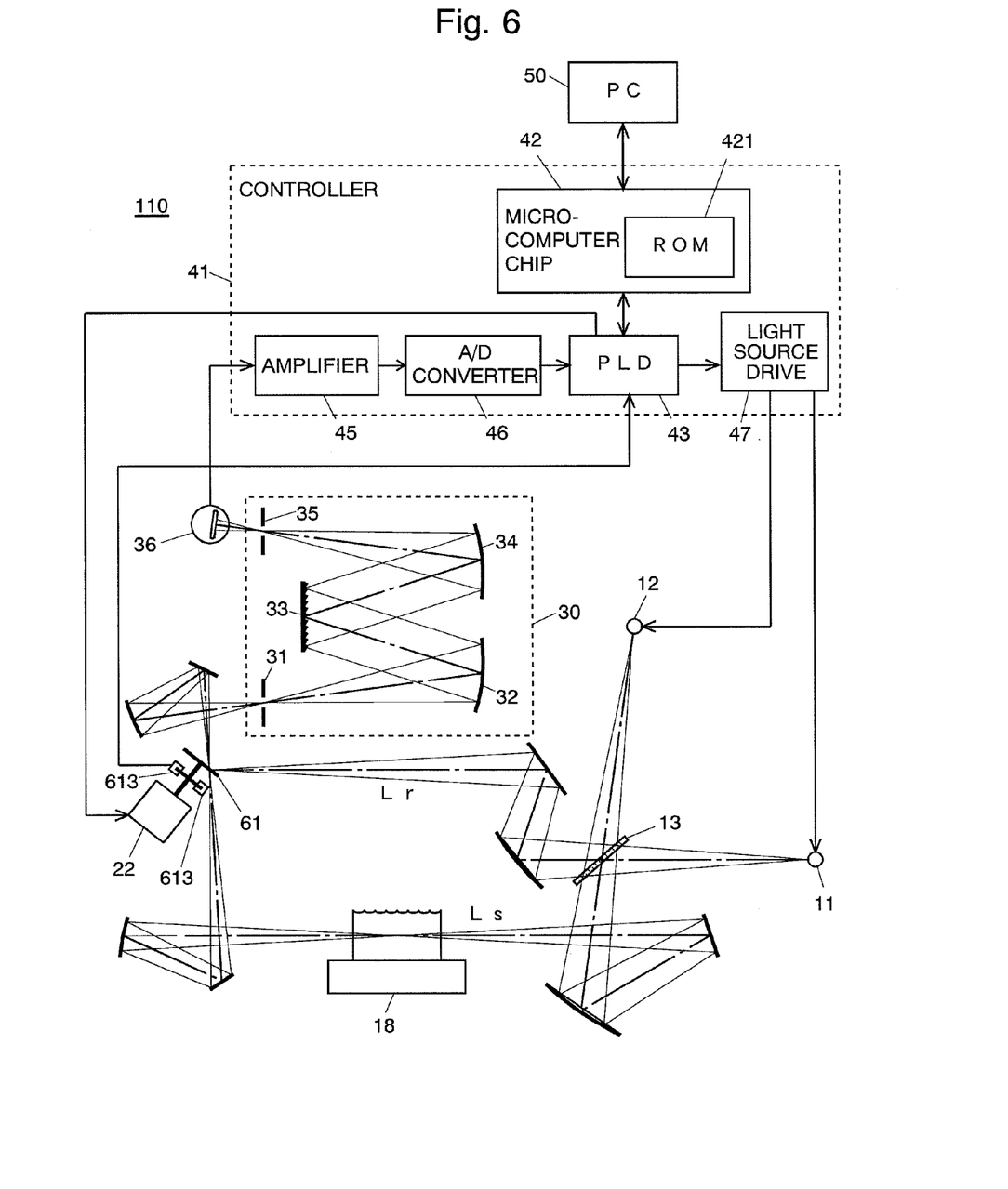
FIG. 6 is a schematic configuration diagram of an atomic absorption spectrophotometer according to one embodiment of the present invention.

Hereinafter, an explanation will be made for an atomic absorption spectrophotometer according to one embodiment of the present invention. FIG. 6 shows a schematic configuration diagram of the atomic absorption spectrophotometer 110 according to the present embodiment. The atomic absorption spectrophotometer 110 has an optical system similar to that of the conventional atomic absorption spectrophotometer 10 which is illustrated in FIG. 1, and is mainly composed of: a hollow cathode (HC) lamp 11; a deuterium (D2) lamp 12; a half mirror 13; an atomization unit 18; a sector mirror 61; an AC motor 22; a photo interrupter 613; a spectroscope 30; a detector 36; and a controller 41. The AC motor 22 is driven by a commercial AC source of 50 Hz or 60 Hz. The spectroscope 30 is composed of: an entrance slit 31; concave spherical mirrors 32 and 34; a plane diffraction grating 33; and an exit slit 35. As the detector 36, a photomultiplier or other device may be used.

The controller 41 is composed of: a microcomputer chip 42 having built-in elements such as a central processing unit (CPU), a read-only memory (ROM) which may be a flash memory, and other electronic circuits including a control circuit of a serial interface used for communication with a random-access memory (RAM) and the personal computer (PC) 50; a programmable logic device (PLD) 43, which is connected to the microcomputer chip 42, for controlling a variety of hardware components; an amplifier 45 for amplifying detection signals generated from the detector 36; an A/D converter 46 for converting the amplified detection signal into a digital signal and sending the digital signal to the PLD 43; and a light source drive 47 for turning ON the HC lamp 11 and D2 lamp 12 as instructed by the PLD 43.

In the ROM 421 inside the microcomputer chip 42, a control program which runs on the CPU of the microcomputer is written. The optimum setting values for the lighting period of the light source and the extraction period of the sampling data are provided for two frequencies (50 Hz and 60 Hz) and two measurement modes (the Non-BGC-Double measurement mode and BGC-D2-Double measurement mode). These values are treated as an internal variable of the control program which runs on the microcomputer chip 42. Hereinafter, the microcomputer chip 42 will be regarded to have the aforementioned control program function as a portion of the chip.

Figure 7A:
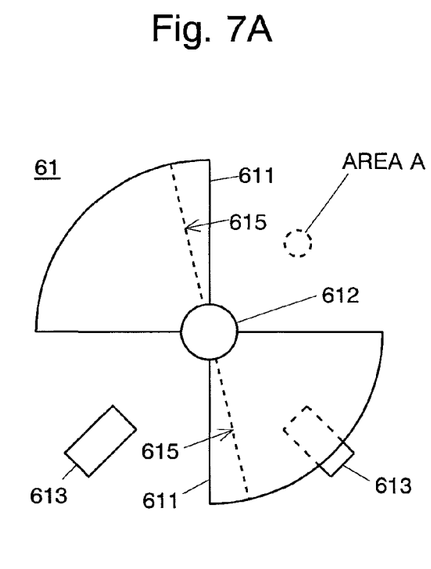
Figure 7B:
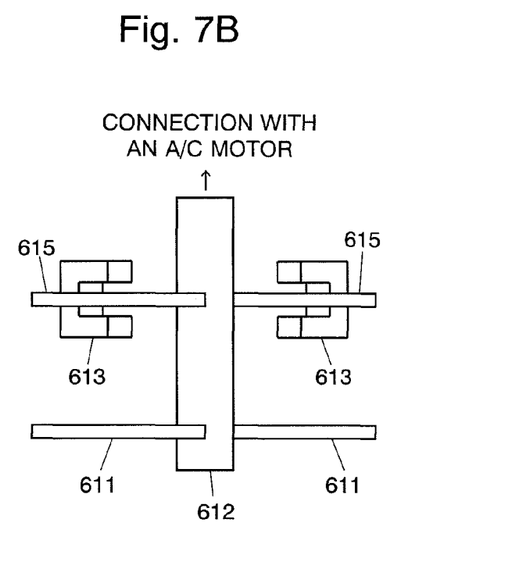
FIG. 7B is a top view of the sector mirror.

FIG. 7A shows a front view of the sector mirror 61 of the present embodiment and FIG. 7B shows a top view thereof. The sector mirror 61 has two sector-shaped mirrors 611, each having a central angle of 90°, symmetrically-placed with respect to a shaft 612. An AC motor 22 is connected to the shaft 612, and the sector mirror 61 rotates around the shaft 612 by the AC motor 22.

The shaft 612 has two sector-shaped timing plates 615 in the position where they substantially overlap the mirror 611, when viewed from the front. The central angle of the timing plate 615 is smaller than that of the mirror 611.

On the rotational course of the timing plate 615, two photo interrupters 613 are placed in such a manner as to sandwich the course. Each photo interrupter 613 generates, as a detection signal, an H level signal while the timing plate 615 exists in the position and an L level signal while the timing plate 615 does not exist.

The angular difference between the central angle of the mirror 611 and that of the timing plate 615 is set to be the angle of rotation of the mirror 611 when the edge of the rotating mirror 611 moves from one edge to the other edge of the area A of the light from the light source in the sector mirror 61. This configuration makes one photo interrupter 613 (which is the right one in FIG. 7A) generate the H level signal only while the mirror 611 is completely off the area A, and the other photo interrupter 613 (which is the left one in FIG. 7A) generate the H level signal only while the mirror 611 completely covers the area A.

Figure 8:
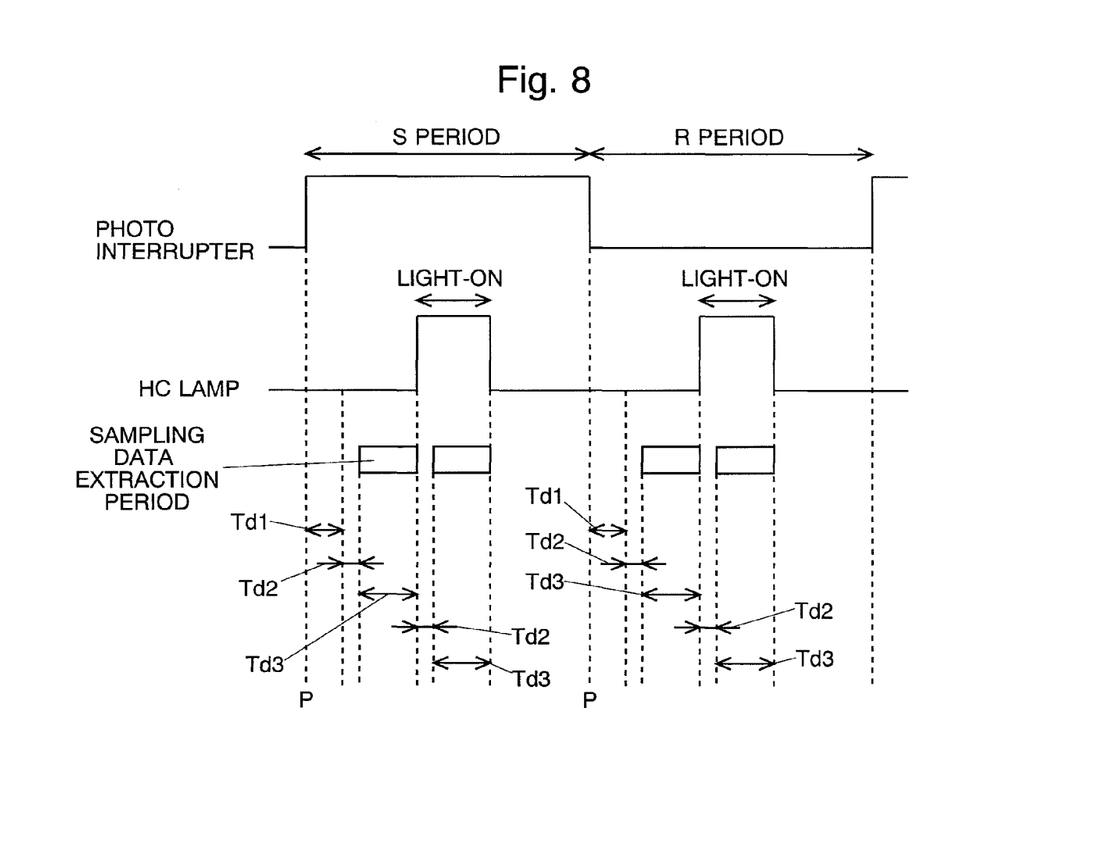
FIG. 8 is a diagram illustrating an example of a blinking manner of the HC lamp and the extraction period of the sampling data in the Non-BGC-Double measurement mode.

The setting values regarding the lighting period of the light source and the extraction period of the sampling data will now be explained with reference to FIG. 8. In this example, only the HC lamp 11 is turned ON and OFF in the Non-BGC-Double measurement mode, and as the setting values, the first, second, and third predetermined periods Td1, Td2, and Td3 are set. Here, the lighting of the light source and the extraction of the sampling data are performed in the following manner. In the present embodiment, the period from the time point when the detection signal of either one of two photo interrupters changes from the L level to H level to the time point when the detection signal of the other photo interrupter changes from the L level to H level is called an S period or R period. The time point when these periods start is called a changing point P. First, the first predetermined period Td1 passes from the changing point P of the detection signal of the photo interrupter 613, and the second predetermined period Td2 passes. Then, from this time point, the sampling data is extracted for the third predetermined period Td3. This is the data with the light source OFF. Next, simultaneously with the termination of the extraction, the HC lamp 11 is turned ON. From the time point after the predetermined period Td2 passes after the lighting of the HC lamp 11, the sampling data is extracted for the third predetermined period Td3. This is the data with the light source ON. On finishing the extraction, the HC lamp 11 is turned OFF. It should be noted that this example is merely an example, and the setting values regarding the lighting period of the light source and the extraction period of the sampling data can be determined in a variety of ways other than the aforementioned manner.

Hereinafter, an operation of the atomic absorption spectrophotometer 110 according to the present embodiment will be explained. In the atomic absorption spectrophotometer 110, at the power-on timing of this apparatus, the AC motor 22 is driven by order of the microcomputer chip 42 to temporarily rotate the sector mirror 61. In accordance with the rotation, the signals of H level and L level are periodically generated from the photo interrupter 613, and the signals arrive at the microcomputer chip 42 via the PLD 43. The microcomputer chip 42 evaluates the length of the S period and R period based on the received signals, and identifies the frequency (50 Hz or 60 Hz) of the commercial power supply. After that, when a measurement mode is selected by a user through the PC 50 or an input unit which is not shown, the microcomputer chip 42 selects a lighting period of the light source and an extraction period of the sampling data, for the identified frequency, between two kinds of values for 50 Hz and 60 Hz memorized and stored as an internal variable of the control program. Then, the microcomputer chip 42 sets the lighting period to the hardware (PLD 43).

Also during the measurement, the detection signals periodically generated from the photo interrupter 613 in accordance with the rotation of the sector mirror 61 are transmitted to the PLD 43. The PLD 43 instructs, based on the changing point P of the received detection signal and the setting value regarding the lighting period of the light source set by the microcomputer chip 42, the light source drive 47 to turn ON or OFF the light source. The light source drive 47 follows the instruction and supplies electric power to the HC lamp 11 and D2 lamp 12 to turn ON and OFF them.

The light emitted from the HC lamp 11 and D2 lamp 12 pass through the half mirror 13, sector mirror 61, spectroscope 30, and other components to enter the detector 36. In the detector 36, the entered light is photoelectric-converted and a detection signal corresponding to the light intensity is generated. The detection signal is amplified in the amplifier 45, converted into a digital signal at predetermined sampling intervals (e.g. every 10 μs) in the A/D converter 46, and the sampling data is sent to the microcomputer chip 42 via the PLD 43.

Based on the changing point P of the detection signal of the photo interrupter 613 and the setting values regarding the extraction period of the sampling data determined by the frequency and measurement mode, the microcomputer chip 42 extracts the data from the received sampling data only for a predetermined period, and records the extracted data in a predetermined data memory. Using the sampling data obtained as just described, the absorbance of the sample can be computed.

In the atomic absorption spectrophotometer 110 according to the present embodiment, the default values for the lighting period of the light source are recorded as internal variables of the control program of the microcomputer chip 42 as previously described. However, the lighting period of the light source can be temporarily changed by rewriting the internal variables by a control command sent from the PC 50. In addition, the extraction period of the sampling data can also be changed by rewriting the internal variables. Since such a rewriting operation can be performed without taking out a circuit board from the apparatus, it is easy to frequently change each setting value, which is advantageous in searching the optimum value for each setting value. The searching operation for each setting value is normally performed not by a user but by a developer of the apparatus.

Figure 9:
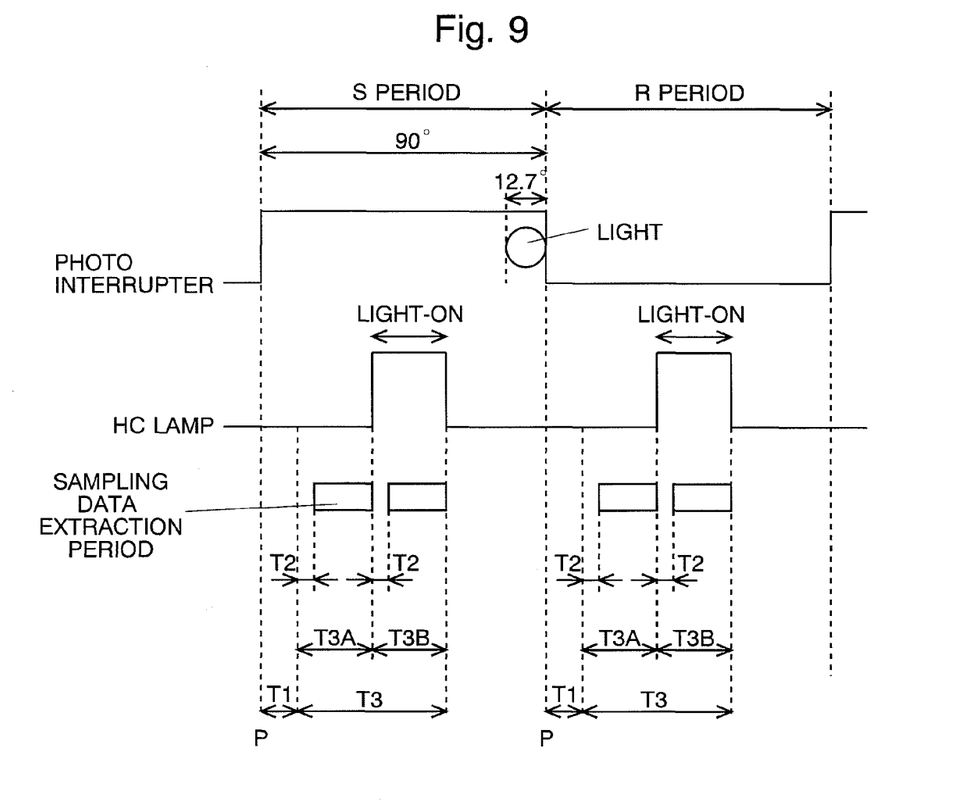
FIG. 9 is a diagram illustrating an example of a blinking manner of the HC lamp and the extraction period of the sampling data in the Non-BGC-Double measurement mode.

Hereinafter, one example of the optimization procedure for each setting value will be explained with reference to FIGS. 9 through 12. In this example, only the HC lamp 11 is turned ON and OFF in the Non-BGC-Double measurement mode. The HC lamp 11 uses Cu (absorbance wavelength: 324.7 nm), the lamp current value which determines the amount of light is 8 mA, and the sampling interval is 10 μs. The setting values T1, T2, and T3 regarding the lighting period of the light source and the extraction period of the sampling data are set as follows:

T1: first cutoff time (×10 μs)
T2: second cutoff time (×10 μs)
T3: data acquisition target time (×10 μs)

Based on T1 through T3, the extraction period of the sampling data is determined in the following manner. As illustrated in FIG. 9, the data acquisition target time T3 starts immediately after the first cutoff time T1 has passed from the changing point P of the detection signal of the photo interrupter 613. The data acquisition target time T3 is the data acquisition target time of the sampling data in the S period and R period, and the former half of the data acquisition target time T3 is the light-off data acquisition target time T3A and the latter half is the light-on data acquisition target time T3B. However, since the amount of light of the light source at start-up is unsteady, the sampling data is not extracted for the second cutoff time T2 from the time point when the light-on data acquisition target time T3B starts, and it is extracted only during the light-on data acquisition target time T3B after the second cutoff time T2. As a matter of the symmetry of data processing, also in the light-off data acquisition target time T3A, the sampling data is not extracted for the second cutoff time T2 from the starting of the light-off data acquisition target time T3A, and it is extracted only during the light-off data acquisition target time T3A after that.

T1 through T3 as just described are optimized in such a manner that the standard deviation (SD value) be the smallest in a base line measurement (i.e. a measurement in the state where no sample is introduced). The SD value is defined by the following procedure: a measurement of absorbance for five minutes is performed seven times and the standard deviation of the averages of absorbance for the seven measurements is obtained. This operation is repeated ten times, and the average value of the ten standard deviations obtained by this operation is treated as the SD value.

Figure 10:
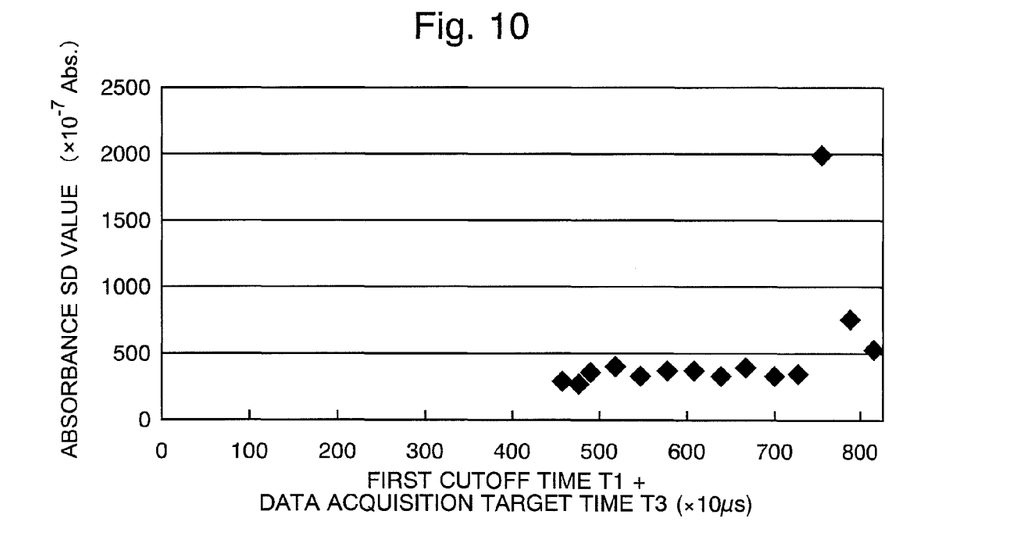
FIG. 10 is a diagram illustrating the relationship between the absorbance SD value and the time in which the first cutoff time T1 and the data acquisition target time T3 are added.

FIG. 10 illustrates the changing manner of the absorbance SD value with T2 (=0 μs) and T3 (=460×10 μs) fixed and T1 changed in the range between 0 and 360×10 μs in the case of the frequency of 60 Hz (S period and R period are 833×10 μs). The horizontal axis of this figure represents the combined time of T1 and T3. This figure shows that even when the combined time of T1 and T3 takes the minimum value (=460× 10 μs), i.e. when T1=0 μs, the absorbance SD value takes the smallest constant value. Therefore, the optimum value for T1 was set to be 0 μs. From around the time point when the combined time of T1 and T3 passes 700×10 μs, the absorbance SD value sharply increases. It can be interpreted that this occurs because the light which reaches the sector mirror 61 has the width corresponding to the rotational angle 12.7° of the sector mirror 61 as a matter of design, and the light enters the end of the mirror 211 around the time point when the aforementioned time passes.

Figure 11:
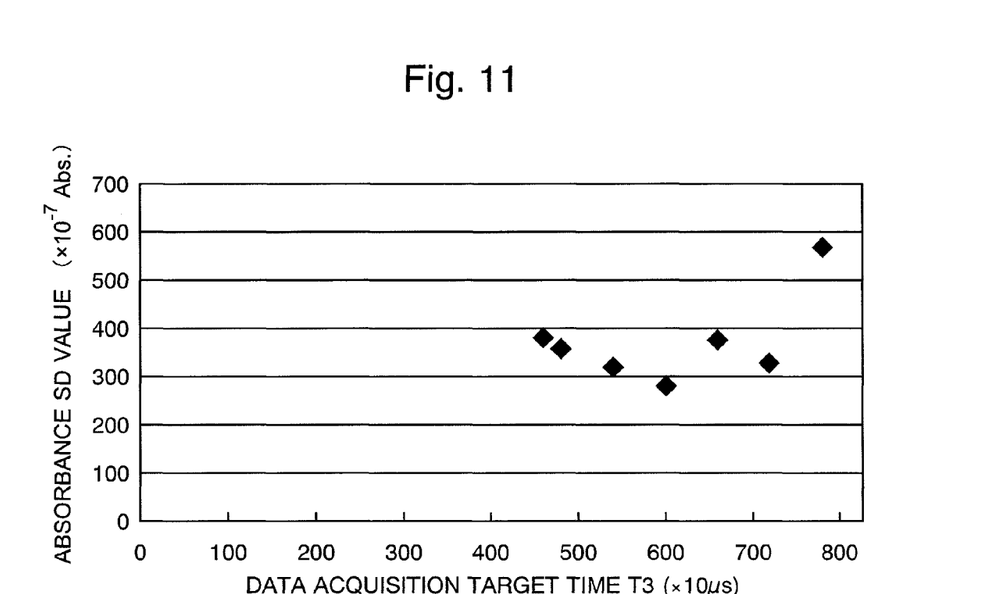
FIG. 11 illustrates the relationship between the absorbance SD value and the data acquisition target time T3.

FIG. 11 illustrates the changing manner of the absorbance SD value with T1 (=0 μs) and T2 (=0 μs) fixed and T3 changed in the range between 460 and 780×10 μs. This figure shows that the absorbance SD value takes the smallest value when T3=600×10 μs. Therefore, the optimum value for T3 was set to be 600×10 μs.

Figure 12:
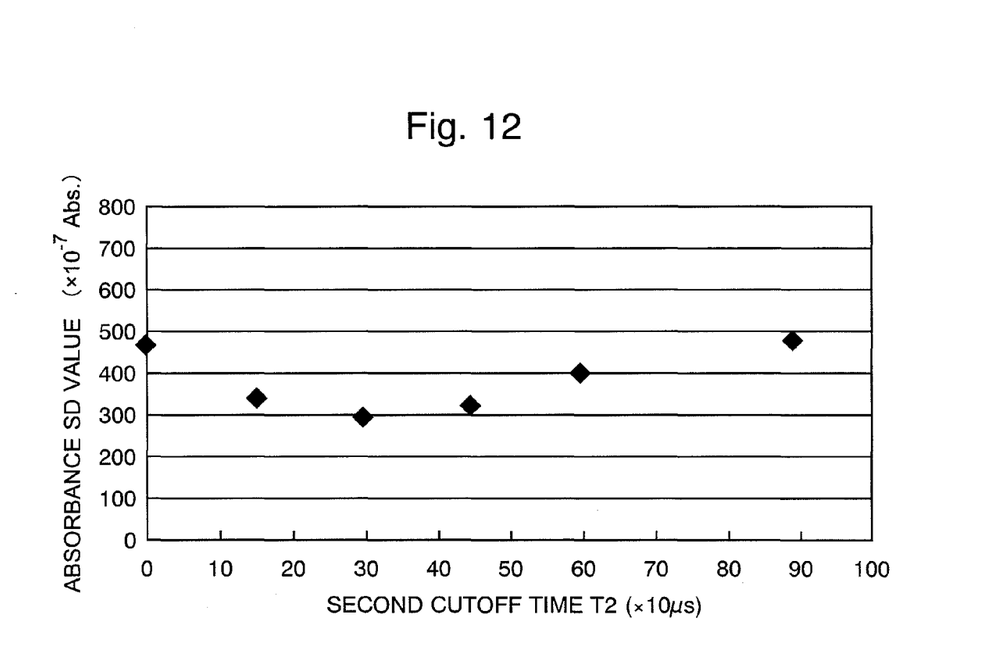
FIG. 12 illustrates the relationship between the absorbance SD value and the second cutoff time T2.

FIG. 12 illustrates the changing manner of the absorbance SD value with T1 (=0 μs) and T3 (=600×10 μs) fixed and T2 changed in the range between 0 and 90×10 μs. This figure shows that the absorbance SD value takes the smallest value when T2=30×10 μs. Therefore, the optimum value for T2 was set to be 30×10 μs. In this figure, the SD values are large at the ends of the measurement range. It can be interpreted that this occurs because of the following: in the case of too small T2, unstable measurement data at the start-up of the light source are used; and in the case of too large T2, the number of pieces of sampling data used for computation is small and the error in statistics becomes large.

These can be summarized as follows. In the present measurement, T1=0 μs, T2=30×10 μs, and T3=600×10 μs, when the absorbance SD value became smallest. In addition, since the S period and R period were 833×10 μs, the data acquisition target time T3 was 600/833=0.72 (72%) to the S period and R period.

Next, a case of the frequency of 50 Hz will be discussed. In this case, since the S period and R period are 1000×10 μs, 1000×0.72=720 (×10 μs) using the aforementioned result is the optimum data acquisition target time T3. Since it can be thought that the second cutoff time T2 depends not on the rotational speed of the sector mirror 61 but only on the electrical characteristics of the circuit, its optimum value can be set to be 30×10 μs, as in the case of 60 Hz. That is, the SD value of the absorbance becomes smallest in this case with the first cutoff time T1=0 μs, the second cutoff time T2=30×10 μs, and the data acquisition target time T3=720×10 μs.

Figure 13:
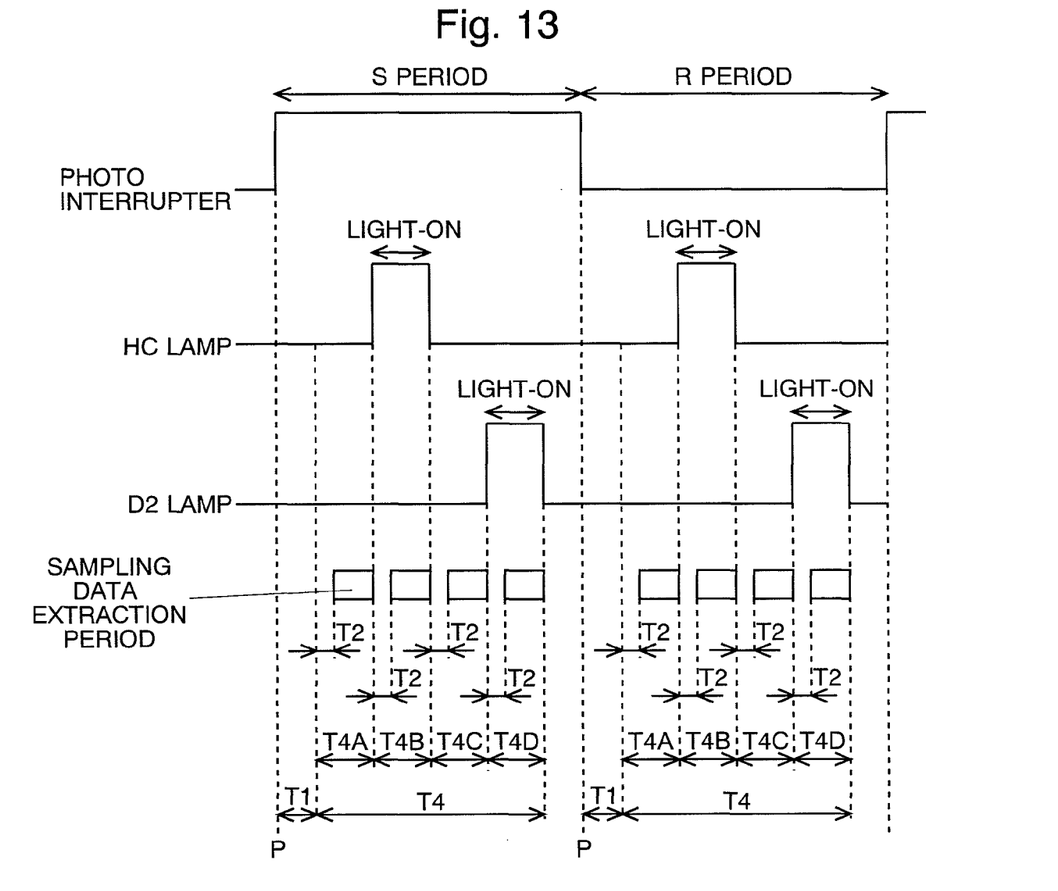
FIG. 13 illustrates an example of the blinking manner of the HC lamp and D2 lamp in the BGC-D2-Double measurement mode, and the extraction period of the sampling data.

Furthermore, a case of the BGC-D2-Double measurement mode will be discussed. In this case, as illustrated in FIG. 13, the second data acquisition target time T4 starts after the first cutoff time T1 has passed from the changing point P of the detection signal of the photo interrupter 613. During the second data acquisition target time T4, in the first quarter is the HC lamp light-off data acquisition target time T4A, the second quarter is the HC lamp light-off data acquisition target time T4B, the third quarter is the D2 lamp light-off data acquisition target time T4C, and the last and fourth quarter is the D2 lamp light-on data acquisition target time T4D. As in the Non-BGC-Double measurement mode which was previously described, the sampling data are not extracted for the second cutoff time T2 after each beginning of T4A through T4D.

The result obtained in the Non-BGC-Double measurement mode can also be applied in this case, and the optimum value of the first cutoff time T1 and second cutoff time T2 is the same as in the previous case (T1=0 μs and T2=30×10 μs). The optimum value of the second data acquisition target time T4 in the case of the frequency of 60 Hz is, since the S period and R period are 833×10 μs, 833×0.72=600 (×10 μs). In the case of the frequency of 50 Hz, the optimum value thereof is, since the S period and R period are 1000×10 μs, 1000×0.72=720 (×10 μs).

These values obtained in this manner are memorized and stored, relating the values to the frequency and measurement mode, as a default value of the internal variable of the control program in the microcomputer chip 42 in order to perform an optimum measurement as previously described.

The aforementioned embodiment is merely an example of the present invention, and a variety of appropriate modifications are possible. For example, instead of periodically turning ON and OFF the light source, the light source may be turned ON and OFF by periodically shutting the light emitted from the light source by a shutter or other configuration. The position where the sample light Ls and reference light Lr reach in the sector mirror does not always have to be the area A shown in FIG. 2, as long as the setting values of the lighting period of the light source and the extraction period of the sampling data are appropriately set. The number of the photo interrupter may be one, and it can be placed on the rotational course of the sector mirror. The memory means for memorizing the setting values may be a memory or other devices outside the microcomputer chip.

What is claimed is:

1. An atomic absorption spectrophotometer comprising:
a) an optical system for dividing a light emitted from a light source into two directions so that one divided light passes through an atomization unit of a sample and an other divided light passes through a space other than the atomization unit, after that introducing each light into a sector mirror rotated by an alternating-current motor so that the divided lights alternately enter a spectroscope, and sending a light separated by the spectroscope to a detector;
b) a light source controller for turning ON the light source for a predetermined lighting period, in synchronization with a rotation of the sector mirror; and
c) a sampling data extractor for extracting sampling data of a detection signal generated from the detector during a predetermined extraction period, in synchronization with the rotation of the sector mirror;
wherein the atomic absorption spectrophotometer comprises:
d) a memory means for memorizing a plurality of setting values of the lighting period and the extraction period, in association with a frequency of an alternating-current power source for driving the alternating-current motor;
e) a frequency identifying means for identifying the frequency of the alternating-current power source; and
f) a lighting/extraction period setting means for reading out a setting value from the memory means, corresponding to the frequency identified by the frequency identifying means, and setting, based on the setting value, the lighting period of the light source and the extraction period of the sampling data.

2. The atomic absorption spectrophotometer according to claim 1, wherein the frequency identifying means identifies the frequency of the alternating-current power source at a power-on timing of the atomic absorption spectrophotometer.

3. The atomic absorption spectrophotometer according to claim 1, wherein the lighting/extraction period setting means changes the lighting period of the light source and the extraction period of the sampling data by an order from a control terminal.

4. The atomic absorption spectrophotometer according to claim 2, wherein the lighting/extraction period setting means changes the lighting period of the light source and the extraction period of the sampling data by an order from a control terminal.

* * * * *